United States Patent [19]
Davis et al.

[11] Patent Number: 5,976,848
[45] Date of Patent: Nov. 2, 1999

[54] METHOD OF IDENTIFYING POTENTIAL FUNGICIDES USING DIHYDROOROTATE DEHYDROGENASE INHIBITION ASSAY

[75] Inventors: George E. Davis, Greenfield; Gary D. Gustafson, Indianapolis; Matthew J. Henry, Indianapolis; Amy J. Smith, Indianapolis; Clive Waldron, Indianapolis, all of Ind.

[73] Assignee: Dow AgroSciences LLC, Indianapolis, Ind.

[21] Appl. No.: 07/828,078

[22] Filed: Jan. 30, 1992

Related U.S. Application Data

[63] Continuation-in-part of application No. 07/562,529, Aug. 3, 1990, abandoned.

[51] Int. Cl.$^6$ ............................................. C12N 9/00
[52] U.S. Cl. ............................................. 435/183; 435/220
[58] Field of Search ................................. 435/183, 220; 436/8

[56] References Cited

U.S. PATENT DOCUMENTS 5,145,843  9/1992  Arnold ...................................... 514/63

FOREIGN PATENT DOCUMENTS 326330  8/1989  European Pat. Off. .

OTHER PUBLICATIONS

Miersch J. Bioactivity & Mode of Action of Some . . . Biomed Biochem Acta 46 (5) pp. 307–315 1987.

Larsen, M.N. and Jensen, K.F., *Eur. J. Biochem.* 151:59–65 (1985).

Davis, G.E. et al., *Phytopathology* 80:1056 (1990); Poster presented at the Annual Meeting of the American Phytopathological Society; Aug. 4–9, 1990; Grand Rapids, MI.

Smith, A.J. et al., *Phytopathology* 80:1053; Poster presented at the Annual Meeting of the American Phytopathological Society; Aug. 4–9, 1990; Grand Rapids, MI.

Gustafson et al., *Curr. Microbiol.* 23:39 (1991).

*Primary Examiner*—Ralph Gitomer
*Attorney, Agent, or Firm*—Donald R. Stuart

[57] ABSTRACT

Dihydroorotate dehydrogenase (DHOD) inhibititon assays are utilized in a method for identifying new fungicides; DHOD inhibitors are useful in fungicidal methods and compositions. Resistance genes that are mutants of the wild-type *Aspergillus nidulans* dihydroorotate dehydrogenase gene have been isolated and found to impart resistance to certain DHOD inhibitors. The resistance genes are useful as selectable markers in fungi. The wild-type gene is also provided.

8 Claims, 3 Drawing Sheets

METHOD OF IDENTIFYING POTENTIAL FUNGICIDES USING DIHYDROOROTATE DEHYDROGENASE INHIBITION ASSAY

RELATED APPLICATIONS

This application is a continuation-in-part of Ser. No. 07/562,529, filed Aug. 3, 1990, now abandoned.

BACKGROUND OF THE INVENTION

Dihydroorotate dehydrogenase (DHOD) is an enzyme in the de novo pyrimidine biosynthetic pathway. Certain anti-cancer compounds have been reported as having inhibition of DHOD as their mode of action. *Biochemical Pharmacology*, Vol. 40, No. 4, pp. 709–714, 1990.

Phenoxyquinolines are a novel class of plant fungicides described in detail in U.S. patent application Ser. No. 07/334,422, filed Apr. 7, 1989, by Wendell Arnold et al. One compound in this series is 8-chloro-4-(2-chloro-4-fluorophenoxy)quinoline (CCFQ). CCFQ completely inhibits the fungal pathogens *Botrytis cinerea* and *Penicillium digitalum* at 50 µg/ml in greenhouse tests. The fungicide has an $IC_{50}$ (concentration that inhibits growth by 50%) of 0.15 µg/ml against *Aspergillus nidulans*. The fungi Cephalosiorium and Neurospora are also sensitive to CCFQ.

We have discovered that the fungicidal activity exhibited by at least some of the phenoxyquinolines, including CCFQ, is a result of their inhibition of DHOD. This is a previously undescribed mode of action for fungicides.

There are few known resistance genes useful as selectable markers in the fungi. The present invention provides new DNA sequences which impart CCFQ resistance to fungi. The DNA sequences comprise mutations in the dihydroorotate dehydrogenase (DHOD) gene of *Aspergillus nidulans*. Also provided is the wild-type DHOD gene, which is useful for preparing other resistance genes.

SUMMARY OF THE INVENTION

One aspect of the present invention is a method for identifying potential fungicides which comprises:
  (a) testing a candidate compound in a DHOD inhibition assay, and
  (b) if the candidate compound is active in the DHOD inhibition assay, testing the compound for activity against fungi.

Another aspect of the invention is a method for identifying potential plant fungicides which comprises testing a candidate compound in a DHOD inhibition assay wherein the assay utilizes DHOD isolated from any of the following plant pathogens: *Pyrenophora teres, Rhynchosporium secalis, Venturia inequalis, Alternaria mali, Rhizoctonia solani,* Fusarium sp., *Leptosphaeria nodorum, Pseudocercosporella herpotrichoides, Pyricularia oryzae, Pyricularia grisea, Phytophthora infestans,* Phytophthora sp., Pythium sp., *Mycosphoerella tritici, Gorticium sasakii.*

Another aspect of the invention is a fungicide method which comprises applying a fungi inhibiting amount of a DHOD inhibitor to the locus it is desired to protect from fungi.

A further aspect of the invention is a fungicide composition comprising a DHOD inhibitor as the active ingredient in combination with a carrier.

Yet an other aspect of the invention is a fungicide composition comprising a DHOD inhibitor in combination with another fungicide.

The present invention provides DNA sequences that impart resistance to the fungicide 8-chloro-4-(2-chloro-4-fluorophenoxy) quinoline (CCFQ). These DNA sequences comprise mutations of the dihydroorotate dehydrogenase gene of *Aspergillus nidulans*. Also provided by the present invention is the wild-type DHOD gene, which is useful to create other mutant genes. The resistance genes are useful as selectable markers in fungi including, but not limited to, Aspergillus, Penicillium and Cehalosorium. Methods for constructing recombinant host cells resistant to CCFQ are also provided by the present invention, as are said recombinant host cells.

The following section provides a more detailed description of the present invention. For purposes of clarity and as an aid in the understanding of the invention the following items are defined below.

ApR—the ampicillin resistance-conferring gene.

CCFQ R—an 8-chloro-4-(2-chloro-4-fluorophenoxy) quinoline resistance gene.

cos—a DNA sequence required for packaging DNA into bacteriophage lambda particles.

Isolated DNA sequence—Any DNA sequence, however constructed or synthesized, which is locationally distinct from its location in genomic DNA. The definition includes the isolated DNA sequence in all its forms other than the natural state. For example, the DNA sequence may be inserted into a plasmid or phage vector or inserted into the genome of the organism from which it came or any other organism.

The following one-letter amino acid codes are used throughout the document.

| Symbol | Meaning |
| --- | --- |
| A | Alanine |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |

BRIEF DESCRIPTION OF THE FIGURES

The restriction site and function maps presented in the accompanying drawings are approximate representations of the recombinant DNA vectors discussed herein. The restriction Site information is not exhaustive; therefore, there may be more restriction sites of a given type on the vector than actually shown on the map.

DETAILED DESCRIPTION OF THE INVENTION

Figure 1:
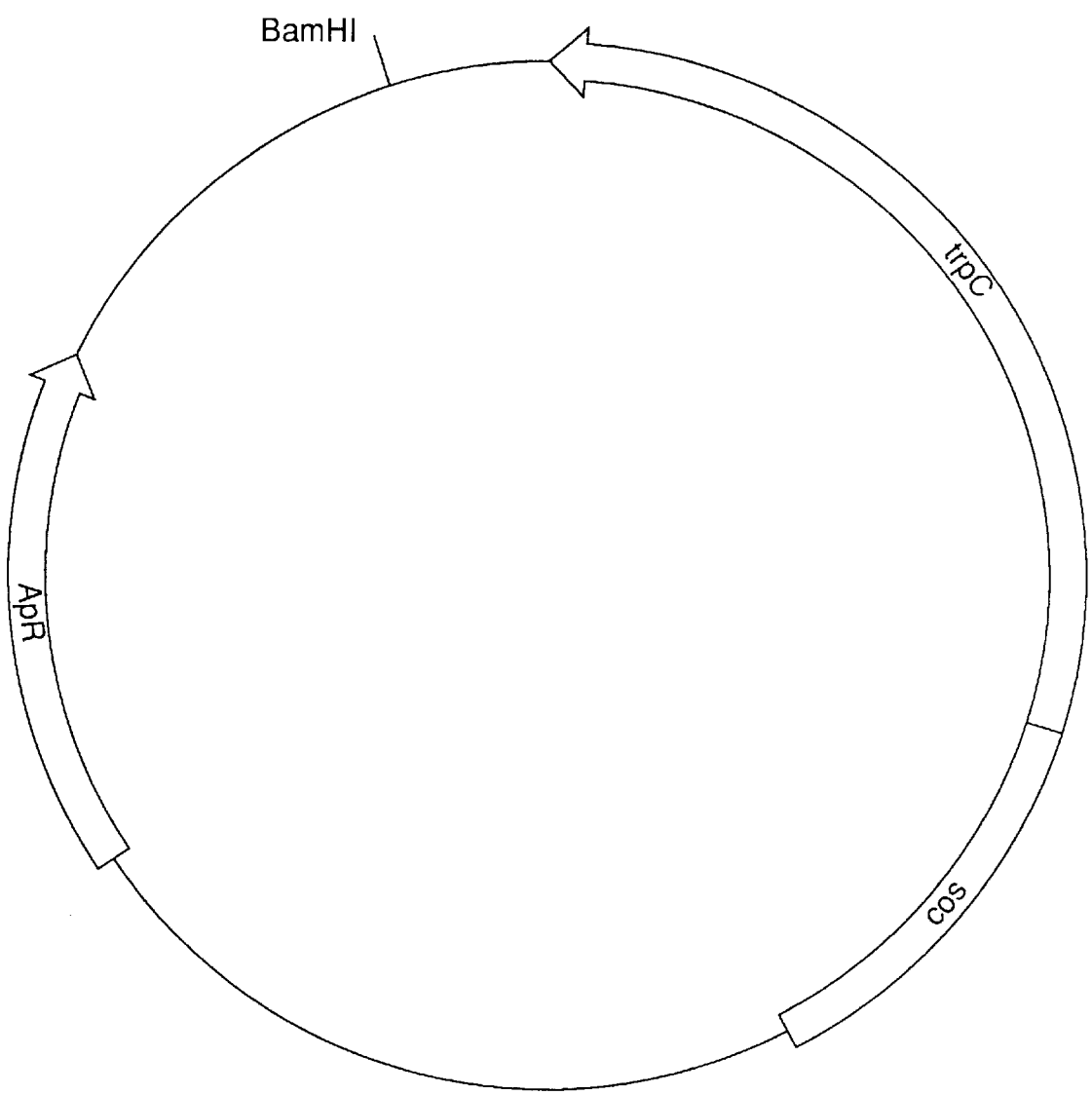
FIG. 1. A restriction site and function map of cosmid pKBY2.

The physiological and biochemical responses caused by the experimental fungicide CCFQ are not characteristic of known modes of action. Treatment of *Aspergillus nidulans* with CCFQ perturbs cell wall synthesis in a non-specific manner, but causes no significant changes in respiration, lipid composition, amino acid content, or protein accumulation. It causes an unusual effect on synthesis of nucleic acids in that incorporation of radiolabelled precursors is stimulated by treatment with CCFQ. The nature of the mode of action for CCFQ was first suggested by growth remediation experiments. Some media supplements overcame growth inhibition by CCFQ. However, only a combination of uracil and a scavenger of free radicals, such as α-tocopherol, gave complete reversal. All these observations are consistent with the primary target of CCFQ being an electron-transferring enzyme in the pyrimidine biosynthetic pathway. The only such enzyme, DHOD, is in fact extremely sensitive to CCFQ in in vitro tests. Moreover, mutant *Aspergillus nidulans* strains that are resistant to CCFQ have been isolated, and the DHOD produced by these strains is resistant to inhibition by CCFQ. Finally, the DNA sequence responsible for imparting resistance to these mutant strains was isolated and was shown to comprise a mutation of the DHOD gene. These results establish DHOD inhibition as the mode of action for CCFQ. This is a novel fungicidal mode of action, and its discovery opens the opportunity to detect novel chemical compounds that attack the same target.

Our method for identifying potential fungicides does not require use of any particular DHOD inhibition assay. A suitable assay is described hereinafter, but those skilled in the art can readily substitute functionally equivalent test methods. For example, although the assay described hereinafter uses DHOD produced by *Pyricularia grisea*, the DHOD produced by other fungi may be substituted. Preferably the DHOD of a commercially significant target fungus, such as *Pyrenophora teres, Rhynchosporium secalis, Venturia inegualis, Alternaria mali, Rhizoctonia solani,* Fusarium sp., *Leptosphaeria nodorum, Pseudocercosporella herpotrichoides, Pyricularia oryzae, Pyricularia grisea, Phytophthora infestans,* Phytophthora sp.,Pythium sp., *Mycosphoerella tritici, Gorticium sasakii.,* is used. Compounds that are active in the DHOD inhibition assay are then tested using any desired fungicide activity test. In this context, "active in the DHOD inhibition assay" means that a measurable reduction in DHOD activity is observed. we have found it convenient in our work to restrict further testing to those compounds that cause at least a 50% reduction in DHOD activity.

Our fungicide method and fungicide composition require use of a "DHOD inhibitor". As used in describing and claiming the fungicide method and fungicide composition, the term "DHOD inhibitor" encompasses any compound that: (a) produces measurable inhibition in a DHOD inhibition assay using DHOD from a target fungus; (b) is not a general enzyme inhibitor, and (c) is not a 4-substituted quinoline, quinazoline, cinnoline, naphthyridine, pyridopyrimidine, thienopyrimidine, furopyrimidine, or other compound that was known to have fungicidal activity prior to the filing date of this application. It should be understood that no fungicide was known to have DHOD inhibition as its mode of action at the time the present invention was made. Applicants invention is not intended to encompass fungicidal use of any previously known fungicide.

Preferred DHOD inhibitors are those which produce at least a measurable reduction in DHOD activity when tested at 10 µg/mL in the Pyricularia grisea DHOD Inhibition Assay described hereinafter.

More preferred DHOD inhibitors are those which produce at least a 25% reduction in DHOD activity when tested at 10 µg/mL in the Pyricularia grisea DHOD Inhibition Assay.

Especially preferred DHOD inhibitors are those which produce at least a 50% reduction in DHOD activity when tested at 10 µg/mL in the Pyricularia grisea DHOD Inhibition Assay.

R. W. Miller has described DHOD isolation and assay methods. *Can. J. Biochem.* 53, 1288 (1975); *Methods in Enzymology*, 51, 63 (1978). The following DHOD inhibition assay is adapted from those described by Miller.

*Pyricularia arisea* DHOD Inhibition Assay

DHOD inhibition is measured by spectrophotometrically observing (at 610 nm) the reduction of dichloroindophenol (DCIP) by electrons liberated when dihydroorotate is oxidized to orotate. Electrons are transferred to DCIP in the reaction mixture via ubiquinone-30. DCIP is a dark blue dye that strongly absorbs at 610 nm and becomes clear when reduced. Rotenone and KCN are added to the reaction mixture to prevent transfer of electrons to DCIP via other pathways.

"Stock reaction mix" for use in the DHOD inhibition assay comprises the following reagents in solution in T-TX100 buffer ("T-TX100 buffer" comprises 50 mM Tris.HCl, pH 7.5 containing 0.1% Triton X100):

| | |
|---|---|
| ubiquinone-30 | 500 μM |
| dihydroorotic acid | 500 μM |
| dichloroindophenol (DCIP) | 250 μM |
| potassium cyanide (KCN) | 43.75 mM |
| rotenone | 150 μM |

"stock control mix" is identical to stock reaction mix, except that the ubiquinone-30 is omitted.

DHOD for use in the assay was obtained as follows.

Cultures of *Pyricularia grisea Sacc*. strain P-2 (ATCC 58061, Tokousbalides and Sisler, 1979) were maintained on oatmeal agar, which was prepared by straining 37.5 g of oatmeal boiled in 1 liter of water through two layers of cheesecloth, then adding 13 g of agar per liter before autoclaving 30 minutes. Oatmeal agar plates were flood-inoculated with conidia or macerated mycelia and incubated at 24° C. for ten days under cool white fluorescent lighting. Conidia were harvested by dislodging with a sterile glass rod in water containing 0.1% Tween 20, then filtered through sterile glass wool. Flasks containing media 56 (Coursen and Sisler, *Amer. J. Bot*. 47, 541 (1960)) supplemented with 2× phosphate and 2% yeast extract were inoculated to provide $1.5\times10^7$ conidia $L^{-1}$. The cultures were incubated at 150 rpm for 38–42 hours at 30° C. Mycelia were collected on miracloth by vacuum filtration and washed twice with cold Tris buffer (50 mM Tris.HCl, pH 7.5).

Harvested mycelia were resuspended in two volumes of Tris buffer. Equal volumes (175 mL) of resuspended mycelia and 0.5 mm diameter glass beads were placed in a 350 mL Beadbeater™ chamber (Biospec Products, Bartlesville, Okla.), Mycelia were broken by operating the Beadbeater for four 30-second cycles with 30-second cooling intervals between cycles. The homogenate was decanted, and the beads washed with approximately one volume of buffer which was added to the homogenate. The pooled homogenate was centrifuged at 3,000×g for 10 min at 4° C. The supernatant was recovered and adjusted to 25 mM $CaCl_2$ by slowly adding solid $CaCl_2.H_2O$. The supernatant was then centrifuged at 30,000×g for 30 minutes at 4° C. The pelleted material was homogenized in a glass/teflon tissue grinder with approximately 150 mL of T-TX100 buffer per liter of pooled homogenate. The homogenate was frozen dropwise in liquid $N_2$ and stored at minus 80° C.

"Dilute DHOD solution" was prepared by diluting one volume of homogenate with four volumes of T-TX100 buffer containing 6.25 mM dihydroorotate. Using this dilution rate gives an activity in the assay of 50–70 mAbs$_{610\,nm}$/min for 5 minutes. The presence of the dihydroorotate is required to maintain satisfactory stability of the enzyme.

Samples (2–3 mg) of compounds to be screened are dissolved in DMSO to obtain a stock sample having a concentration of 1 mg/mL for each compound.

The assay is preferably conducted using Falcon® 96-well, flat bottom polystyrene plates. These plates have 96 wells arrayed in 12 columns and 8 rows. To each well in columns 2, 5, and 8 of the 96 well plate is added 20 μL of a different stock sample. Accordingly, 24 different compounds can be tested on one plate. Then 180 μL of T-TX100 buffer is added to each of the wells in columns 2, 5, and 8, resulting in a 10-fold dilution from the initial concentration of the stock sample.

To each well in columns 3,4,6,7,9, and 10 of the plate is added 80 μL of stock reaction mix. Then, for each row, 20 μL of diluted test solution from the well in column 2 are transferred to each of the two wells in columns 3 and 4 of the same row. The contents of each well are mixed. Similarly, for each row, 20 μL of diluted test solution from the well in column 5 are transferred to each of the two wells in columns 6 and 7, and 20 μL of diluted test solution from the well in column 8 are transferred to each of the two wells in columns 9 and 10. At this point, each of the wells in columns 3,4,6,7,9, and 10 contains 100 μL of solution with a concentration of 20 μg/mL of test compound. Columns 3 and 4 contain duplicate samples for the first eight compounds, columns 6 and 7 contain duplicate samples for the second eight compounds, and columns 9 and 10 contain duplicate samples for the remaining eight compounds.

The inhibition of DHOD by CCFQ may desirably be used to standardize the effects of other test compounds on DHOD activity. For this purpose, we typically include CCFQ at concentration of 10, 5, and 1 μg/mL in DMSO (resulting in final concentration of 0.1, 0.05, and 0.01 μg/mL) as the last three compounds on the plate.

The wells in column 1 of the plate are used for determining background and total activity. 20 μL of T-TX100 buffer is pipetted into each well in column 1 of the plate. Then, to each well in the first four rows (A,B,C, and D) of column 1 are added 80 μL of stock control mix (background). To each well in the last four rows of column 1 (E,F,G,and H) are added 80 μL of stock reaction mix (total).

Preparation of the plates is preferably automated, using a Biomek 1000 Automated Laboratory Workstation (Beckman) to dilute the stock compounds and add appropriate volumes of reaction solutions and compounds to the individual wells of the 96-well microtiter plate.

The assay is initiated by adding 100 μL of dilute DHOD solution to each well, which is conveniently done using an Eppendorf 8-channel dispenser. After this solution is added, the concentration of test compound in each well is 10 μg/mL. The contents of each well on the plate is mixed, and changes in absorbance at 610 nm are recorded every 10 seconds for 5 minutes using the THERMO$_{max}$™ (Molecular Devices) plate reader(set at 30° C. incubation temperature).

The rate of absorbance change per minute (mAbs$_{610\,nm}$/min) due to reduction of DCIP is then calculated for each sample and the background controls. A plot of absorbance versus time for each well yields a downward sloping line, reflecting decreased absorbance as the DCIP is reduced. Under the conditions of the assay described above, the plot is essentially linear. Compounds that inhibit DHOD reduce the reaction rate and result in a linear plot with a reduced slope. Percent activity is calculated using the following formula $$\% \text{ activity} = 100 \times \frac{(\text{rate}_{\text{test}} - \text{rate}_{\text{background}})}{(\text{rate}_{\text{total}} - \text{rate}_{\text{background}})}$$

where rate$_{background}$ is given by the slope of the curve obtained for cells in the first four wells of column 1, rate$_{total}$ refers to the slope of the curve obtained for cells in the second four rows of column 1, and rate$_{test}$ refers to the slope obtained for the wells containing test compound.

We have found a strong correlation between activity of a compound in the DHOD assay and fungitoxicity.

The present invention is directed to fungicidal use of compounds that inhibit DHOD, as opposed to fungicidal use of compounds that inhibit enzymes generally. An example of a compound that inhibits enzymes generally is maneb. To eliminate the possibility that a compound active in the DHOD assay is a general enzyme inhibitor, the active compound can be tested in a second enzyme assay. A suitable assay for this purpose is the *E. Coli* alkaline phosphatase assay described by Garen and Levinthal, *Biochim. Biophys.* ACTA, 38, 470 (1960). If the compound is not active in the second enzyme assay, it may be concluded that the compound does not inhibit enzymes generally.

Biological efficacy of a fungicidal compound in whole organisms is influenced by many factors, including not only intrinsic activity of the compound, i.e. efficiency of its interaction with the target molecule, but also stability of the compound and ability of the compound to be translocated to the target site. The DHOD inhibition assay measures the intrinsic activity of the compound. It will be appreciated by those skilled in the art that once a potential fungicide is detected using the DHOD assay, conventional techniques must be used to determine the usefulness of the compound in various environments.

As used herein, the term "fungi inhibiting amount of DHOD inhibitor" refers to an amount of DHOD inhibitor sufficient to kill or inhibit the fungi it is desired to control.

When employed in the treatment of plant fungal diseases, the DHOD inhibitors are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 1 to 500 ppm being preferred. The exact concentration of compound required varies with the fungal disease to be controlled, the type formulation employed, the method of application, the particular plant species, climate conditions and the like. A suitable application rate is typically in the range from 100 to 1000 g/ha The compounds of the invention may also be used to protect stored grain and other non-plant loci from fungal infestation.

Compositions

When used on plants, DHOD inhibitors are applied in the form of compositions which are important embodiments of the invention, and which comprise a DHOD inhibitor as active ingredient in combination with a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, for example the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Fungicides are generally applied in the form of a dispersion of the active ingredient in a liquid carrier. It is conventional to refer to application rates in terms of the concentration of active ingredient in the carrier. The most widely used carrier is water.

DHOD inhibitors can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The present invention provides DNA compounds comprising isolated DNA sequences encoding 8-chloro-4-(2-chloro-4-fluorophenoxy) quinoline resistance genes. The isolated DNA sequences comprise mutations of the dihydroorotate dehydrogenase gene of *Aspergillus nidulans*.

The DNA sequences are useful as selectable markers in fungi, especially Aspergillus, Penicillium, and Cephalosporium. Also provided by the present invention are methods for constructing a recombinant host cell resistant to 8-chloro-4-(2-chloro-4-fluoro-phenoxy) quinoline and the recombinant host cells so constructed. Finally, the dihydroorotate dehydrogenase gene of *Aspergillus nidulans* is also a part of the present invention.

The fungicide 8-chloro-4-(2-chloro-4-fluoro-phenoxy) quinoline (CCFQ) completely inhibits the growth of such fungal pathogens as *Botrytis cinerea* and *Penicillium digitalum*. CCFQ also inhibits the growth of Aspergillus, Neurospora and Cephalosporium. DNA sequences which impart resistance to CCFQ are useful as selectable markers in fungi. Such DNA sequences are mutants of the wild-type dihydroorotate dehydrogenase (DHOD) gene of *Aspergillus nidulans*. The wild-type DHOD gene is useful to make other resistance genes.

CCFQ is made by the procedures described in European Patent Publication No. 326330, published Aug. 2, 1989. For use with Aspergillus, it is included in the media at 2.5 $\mu$g/ml.

Host cells comprising the wild-type DHOD gene are sensitive to CCFQ. The DNA sequence of this gene is below. All DNA sequences herein are depicted from left to right in the 5'→3' orientation.

| | | | | |
|---|---|---|---|---|
| 1 ATGGCTACGA | ATTCTTTCCG | AAAACTCACT | TTTTCAGGAG | CCTCCCGTCT |
| 51 GGGTGGTTGT | CGCCGTCTCC | CACTAACCTG | CAGACAACTT | CGATTCGCCT |
| 101 CCGACAGCGG | AGCCGCAGCG | GCAACTACAA | AAGCAACGGC | CGAATCAGCA |
| 151 GCCGAGTCAG | CTAGTATAAA | CGTCAAAGAG | GCACCCAAAA | AGGCCGGACG |
| 201 GGGCCTGCGG | CGCACGGTCC | TGGGAACGTC | GTTGGCGCTG | ACGCTGCTGG |
| 251 TTGGATATGT | CTACGGGACG | GACACCCGGG | CGAGTGTGCA | TCGGTACGGT |
| 301 GTTGTGCCGC | TGATTAGAGC | ATTGTATCCT | GATGCGGAAG | ATGCGCATCA |
| 351 TATTGGTGTC | GATACTTTAA | AGATGCTGTA | TAAGTATGGT | CTGCATCCAA |
| 401 GGGAACGGGG | GGATCCGGAT | GGAGATGGGG | CGCTGGCGAC | AGAGGTGGGT |
| 451 GGTCTTTTAT | TGTGATGGAA | GTTAAGGCCC | TAATACTTAT | GGCGGATAGG |
| 501 TCTTTGGGTA | TACACTGTCA | AACCCAATTG | GCATATCGGG | CGGCCTGGAC |
| 551 AAGCATGCTG | AGATCCCTGA | TCCGCTGTTC | GCGATCGGTC | CTGCCATTGT |
| 601 CGAAGTCGGG | GGTACGACAC | CCTTACCACA | GGATGGTAAC | CCGCGTCCTC |
| 651 GCGTATTCCG | ACTTCCATCA | CAGAGAGCGA | TGATAAACCG | GTACGGCCTC |
| 701 AACTCCAAAG | GCGCAGATCA | CATGGCAGCT | ATCTTGGAGC | AACGAGTACG |
| 751 CGATTTTGCC | TACGCAAACG | GATTTGGGGC | ATACGATGCG | GCTAAGCAGC |
| 801 GTGTATTGGA | CGGCGAAGCT | GGTGTGCCAC | CAGGTAGTCT | TCAGCCTGGT |
| 851 AAGCTTTTAG | CTGTCCAAGT | GGCAAAGAAC | AAGGCCACTC | CTGACGGCGA |
| 901 CATTGAAGCC | ATCAAGCGCG | ACTATGTGTA | TTGCGTGGAC | CGTGTGGCCA |
| 951 AATACGCTGA | TATTCTTGTT | GTGAATGTAT | CGAGCCCCAA | CACACCCGGT |
| 1001 CTCCGTGACC | TTCAAGCCAC | TGCCCCGCTC | ACAGCTATCT | TGAGTGCTGT |
| 1051 CGTTGGCGCG | GCAAAGAGCG | TGAACCGCAA | GACCAAACCA | TATGTTATGG |
| 1101 TCAAGGTCAG | TCCGGATGAA | GACTCAGATG | AACAAGTCTC | TGGTATCTGC |
| 1151 GACGCCGTCC | GAGCATCCGG | TGTCGACGGA | GTGATTGTCG | GAAACACAAC |
| 1201 AAACCGTCGC | CCCGACCCTA | TACCCCAAGG | TTACACTCTT | CCGGCCAAGG |
| 1251 AGCAGGCAAC | GTTGAAAGAA | ACCGGCGGGT | ATTCAGGTCC | ACAGCTGTTC |
| 1301 GATCGCACAG | TGGCCCTTGT | GGCTCGGTAC | CGCTCCATGC | TGGATGCGGA |
| 1351 GTCGGAAACG | GCCGGATCCG | CCAAGGATTC | TGGAAGCGCC | AAGCGGACTG |
| 1401 CAGAGCCAGG | CTCGGAAAC | GTTCCTCCTG | TGGAAGCGCC | AAGCGGACTG |
| 1451 CCGCGCAAG | TTATCTTCGC | TTCGGGTGGT | ATCACCAACG | GGAAGCAGGC |
| 1501 TCACGCTGTT | TTAGACACAG | GGGCATCTGT | TGCCATGATG | TACACCGGTG |
| 1551 TGGTCTATGG | TGGCGTCGGC | ACTGTCACTC | GAGTGAAGCA | AGAACTTCGA |
| 1601 ACGGCGAAAA | AGGAG | | | |

The beginning and end of the single intron are marked with asterisks at the G at position 445 and the G at position 499 respectively.

The sequence of the gene with the intron removed

| | | | | |
|---|---|---|---|---|
| 1 ATGGCTACGA | ATTCTTTCCG | AAAACTCACT | TTTTCAGGAG | CCTCCCGTCT |
| 51 GGGTGGTTGT | CGCCGTCTCC | CACTAACCTG | CAGACAACTT | CGATTCGCCT |
| 101 CCGACAGCGG | AGCCGCAGCG | GCAACTACAA | AAGCAACGGC | CGAATCAGCA |
| 151 GCCGAGTCAG | CTAGTATAAA | CGTCAAAGAG | GCACCCAAAA | AGGCCGGACG |
| 201 GGGCCTGCGG | CGCACGGTCC | TGGGAACGTC | GTTGGCGCTG | ACGCTGCTGG |
| 251 TTGGATATGT | CTACGGGACG | GACACCCGGG | CGAGTGTGCA | TCGGTACGGT |
| 301 GTTGTGCCGC | TGATTAGAGC | ATTGTATCCT | GATGCGGAAG | ATGCGCATCA |
| 351 TATTGGTGTC | GATACTTTAA | AGATGCTGTA | TAAGTATGGT | CTGCATCCAA |
| 401 GGGAACGGGG | GGATCCGGAT | GGAGATGGGG | CGCTGGCGAC | AGAGGTCTTT |
| 451 GGGTATACAC | TGTCAAACCC | AATTGGCATA | TCGGGCGGCC | TGGACAAGCA |
| 501 TGCTGAGATC | CCTGATCCGC | TGTTCGCGAT | CGGTCCTGCC | ATTGTCGAAG |
| 551 TCGGGGGTAC | GACACCCTTA | CCACAGGATG | GTAACCCGCG | TCCTCGCGTA |
| 601 TTCCGACTTC | CATCACAGAG | AGCGATGATA | AACCGGTACG | GCCTCAACTC |
| 651 CAAAGGCGCA | GATCACATGG | CAGCTATCTT | GGAGCAACGA | GTACGCGATT |
| 701 TTGCCTACGC | AAACGGATTT | GGGGCATACG | ATGCGGCTAA | GCAGCGTGTA |
| 751 TTGGACGGCG | AAGCTGGTGT | GCCACCAGGT | AGTCTTCAGC | CTGGTAAGCT |
| 801 TTTAGCTGTC | CAAGTGGCAA | AGAACAAGGC | CACTCCTGAC | GGCGACATTG |
| 851 AAGCCATCAA | GCGCGACTAT | GTGTATTGCG | TGGACCGTGT | GGCCAAATAC |
| 901 GCTGATATTC | TTGTTGTGAA | TGTATCGAGC | CCCAACACAC | CCGGTCTCCG |
| 951 TGACCTTCAA | GCCACTGCCC | CGCTCACAGC | TATCTTGAGT | GCTGTCGTTG |
| 1001 GCGCGGCAAA | GAGCGTGAAC | CGCAAGACCA | AACCATATGT | TATGGTCAAG |
| 1051 GTCAGTCCGG | ATGAAGACTC | AGATGAACAA | GTCTCTGGTA | TCTGCGACGC |
| 1101 CGTCCGAGCA | TCCGGTGTCG | ACGGAGTGAT | TGTCGGAAAC | ACAACAAACC |
| 1151 GTCGCCCCGA | CCCTATACCC | CAAGGTTACA | CTCTTCCGGC | CAAGGAGCAG |
| 1201 GCAACGTTGA | AAGAAACCGG | CGGGTATTCA | GGTCCACAGC | TGTTCGATCG |
| 1251 CACAGTGGCC | CTTGTGGCTC | GGTACCGCTC | CATGCTGGAT | GCGGAGTCGG |
| 1301 AAACGGCCGG | ATCCGCCAAG | GATTCAGCAG | CGACCATAGC | GCAAACAGAG |
| 1351 CCAGGCTCGG | AAAACGTTCC | TCCTGTGGAA | GCGCCAAGCG | GACTGCCGCG |
| 1401 CAAAGTTATC | TTCGCTTCGG | GTGGTATCAC | CAACGGGAAG | CAGGCTCACG |
| 1451 CTGTTTTAGA | CACAGGGGCA | TCTGTTGCCA | TGATGTACAC | CGGTGTGGTC |
| 1501 TATGGTGGCG | TCGGCACTGT | CACTCGAGTG | AAGCAAGAAC | TTCGAACGGC |
| 1551 GAAAAGGAG | | | | |

The above DNA sequences encode the DHOD enzyme, which has the amino acid sequence:

| 1 | MATNSFRKLT | FSGASRLGGC | RRLPLTCRQL | RFASDSGAAA | ATTKATAESA |
|---|---|---|---|---|---|
| 51 | AESASINVKE | APKKAGRGLR | RTVLGTSLAL | TLLVGYVYGT | DTRASVHRYG |
| 101 | VVPLIRALYP | DAEDAHHIGV | DTLKMLYKYG | LHPRERGDPD | GDGALATEVF |
| 151 | GYTLSNPIGI | SGGLDKHAEI | PDPLFAIGPA | IVEVGGTTPL | PQDGNPRPRV |
| 201 | FRLPSQRAMI | NRYGLNSKGA | DHMAAILEQR | VRDFAYANGF | GAYDAAKQRV |
| 251 | LDGEAGVPPG | SLQPGKLLAV | QVAKNKATPD | GDIEAIKRDY | VYCVDRVAKY |
| 301 | ADILVVNVSS | PNTPGLRDLQ | ATAPLTAILS | AVVGAAKSVN | RKTKPYVNVK |
| 351 | VSPDEDSDEQ | VSGICDAVRA | SGVDGVIVGN | TTNRRPDPIP | QGYTLPAKEQ |
| 401 | ATLKETGGYS | GPQLFDRTVA | LVARYRSMLD | AESETAGSAK | DSAATIAQTE |
| 451 | PGSENVPPVE | APSGLPRKVI | FASGGITNGK | QAHAVLDTGA | SVAMMYTGVV |
| 501 | YGGVGTVTRV | KQELRTAKKE | | | |

Two mutations of the DHOD gene have been isolated which impart resistance to CCFQ. The preferred mutation changes the thymidyl residue at position 599 of the intron-less coding sequence and position 654 of the intron-containing sequence to an adenyl residue. The resultant amino acid change at position 200 is from valine to glutamic acid. The DNA sequence of the preferred resistance gene is:

| 1 | ATGGCTACGA | ATTCTTTCCG | AAAACTCACT | TTTTCAGGAG | CCTCCCGTCT |
|---|---|---|---|---|---|
| 51 | GGGTGGTTGT | CGCCGTCTCC | CACTAACCTG | CAGACAACTT | CGATTCGCCT |
| 101 | CCGACAGCGG | AGCCGCAGCG | GCAACTACAA | AAGCAACGGC | CGAATCAGCA |
| 151 | GCCGAGTCAG | CTAGTATAAA | CGTCAAAGAG | GCACCCAAAA | AGGCCGGACG |
| 201 | GGGCCTGCGG | CGCACGGTCC | TGGGAACGTC | GTTGGCGCTG | ACGCTGCTGG |
| 251 | TTGGATATGT | CTACGGGACG | GACACCCGGG | CGAGTGTGCA | TCGGTACGGT |
| 301 | GTTGTGCCGC | TGATTAGAGC | ATTGTATCCT | GATGCGGAAG | ATGCGCATCA |
| 351 | TATTGGTGTC | GATACTTTAA | AGATGCTGTA | TAAGTATGGT | CTGCATCCAA |
| 401 | GGGAACGGGG | GGATCCGGAT | GGAGATGGGG | CGCTGGCGAC | AGAGGTGGGT |
| 451 | GGTCTTTTAT | TGTGATGGAA | GTTAAGGCCC | TAATACTTAT | GGCGGATAGG |
| 501 | TCTTTGGGTA | TACACTGTCA | AACCCAATTG | GCATATCGGG | CGGCCTGGAC |
| 551 | AAGCATGCTG | AGATCCCTGA | TCCGCTGTTC | GCGATCGGTC | CTGCCATTGT |
| 601 | CGAAGTCGGG | GGTACGACAC | CCTTACCACA | GGATGGTAAC | CCGCGTCCTC |
| 651 | GCGAATTCCG | ACTTCCATCA | CAGAGAGCGA | TGATAAACCG | GTACGGCCTC |
| 701 | AACTCCAAAG | GCGCAGATCA | CATGGCAGCT | ATCTTGGAGC | AACGAGTACG |
| 751 | CGATTTTGCC | TACGCAAACG | GATTTGGGGC | ATACGATGCG | GCTAAGCAGC |
| 801 | GTGTATTGGA | CGGCGAAGCT | GGTGTGCCAC | CAGGTAGTCT | TCAGCCTGGT |
| 851 | AAGCTTTTAG | CTGTCCAAGT | GGCAAAGAAC | AAGGCCACTC | CTGACGGCGA |
| 901 | CATTGAAGCC | ATCAAGCGCG | ACTATGTGTA | TTGCGTGGAC | CGTGTGGCCA |
| 951 | AATACGCTGA | TATTCTTGTT | GTGAATGTAT | CGAGCCCCAA | CACACCCGGT |
| 1001 | CTCCGTGACC | TTCAAGCCAC | TGCCCCGCTC | ACAGCTATCT | TGAGTGCTGT |
| 1051 | CGTTGGCGCG | GCAAAGAGCG | TGAACCGCAA | GACCAAACCA | TATGTTATGG |
| 1101 | TCAAGGTCAG | TCCGGATGAA | GACTCAGATG | AACAAGTCTC | TGGTATCTGC |
| 1151 | GACGCCGTCC | GAGCATCGG | TGTCGACGGA | GTGATTGTCG | GAAACACAAC |
| 1201 | AAACCGTCGC | CCCGACCCTA | TACCCCAAGG | TTACACTCTT | CCGGCCAAGG |
| 1251 | AGCAGGCAAC | GTTGAAAGAA | ACCGGCGGGT | ATTCAGGTCC | ACAGCTGTTC |
| 1301 | GATCGCACAG | TGGCCCTTGT | GGCTCGGTAC | CGCTCCATGC | TGGATGCGGA |
| 1351 | GTCGGAAACG | GCCGGATCCG | CCAAGGATTC | AGCAGCGACC | ATAGCGCAAA |
| 1401 | CAGAGCCAGG | CTCGGAAAAC | GTTCCTCCTG | TGGAAGCGCC | AAGCGGACTG |
| 1451 | CCGCGCAAAG | TTATCTTCGC | TTCGGGTGGT | ATCACCAACG | GGAAGCAGGC |
| 1501 | TCACGCTGTT | TTAGACACAG | GGGCATCTGT | TGCCATGATG | TACACCGGTG |
| 1551 | TGGTCTATGG | TGGCGTCGGC | ACTGTCACTC | GAGTGAAGCA | AGAACTTCGA |
| 1601 | ACGGCGAAAA | AGGAG | | | |

This DNA sequence is comprised by plasmid pGAR150, available from the NRRL, (Northern Regional Research Center (NRRL), Agricultural Research Service, U.S. Department of Agriculture, Peoria, Ill. 61604) under accession number NRRL B-18692. Other DNA sequences of the invention may be derived from pGAR150 by well-known mutagenesis techniques, including site-specific and deletion mutagenesis. The coding sequence of the preferred resistance gene (with the intron removed) is:

| 1 | ATGGCTACGA | ATTCTTTCCG | AAAACTCACT | TTTTCAGGAG | CCTCCCGTCT |
|---|---|---|---|---|---|
| 51 | GGGTGGTTGT | CGCCGTCTCC | CACTAACCTG | CAGACAACTT | CGATTCGCCT |
| 101 | CCGACAGCGG | AGCCGCAGCG | GCAACTACAA | AAGCAACGGC | CGAATCAGCA |
| 151 | GCCGAGTCAG | CTAGTATAAA | CGTCAAAGAG | GCACCCAAAA | AGGCCGGACG |

```
 201 GGGCCTGCGG  CGCACGGTCC  TGGGAACGTC  GTTGGCGCTG  ACGCTGCTGG
 251 TTGGATATGT  CTACGGGACG  GACACCCGGG  CGAGTGTGCA  TCGGTACGGT
 301 GTTGTGCCGC  TGATTAGAGC  ATTGTATCCT  GATGCGGAAG  ATGCGCATCA
 351 TATTGGTGTC  GATACTTTAA  AGATGCTGTA  TAAGTATGGT  CTGCATCCAA
 401 GGGAACGGGG  GGATCCGGAT  GGAGATGGGG  CGCTGGCGAC  AGAGGTCTTT
 451 GGGTATACAC  TGTCAAACCC  AATTGGCATA  TCGGGCGGCC  TGGACAAGCA
 501 TGCTGAGATC  CCTGATCCGC  TGTTCGCGAT  CGGTCCTGCC  ATTGTCGAAG
 551 TCGGGGGTAC  GACACCCTTA  CCACAGGATG  GTAACCCGCG  TCCTCGCGAA
 601 TTCCGACTTC  CATCACAGAG  AGCGATGATA  AACCGGTACG  GCCTCAACTC
 651 CAAAGGCGCA  GATCACATGG  CAGCTATCTT  GGAGCAACGA  GTACGCGATT
 701 TTGCCTACGC  AAACGGATTT  GGGGCATACG  ATGCGGCTAA  GCAGCGTGTA
 751 TTGGACGGCG  AAGCTGGTGT  GCCACCAGGT  AGTCTTCAGC  CTGGTAAGCT
 801 TTTAGCTGTC  CAAGTGGCAA  AGAACAAGGC  CACTCCTGAC  GGCGACATTG
 851 AAGCCATCAA  GCGCGACTAT  GTGTATTGCG  TGGACCGTGT  GGCCAAATAC
 901 GCTGATATTC  TTGTTGTGAA  TGTATCGAGC  CCCAACACAC  CCGGTCTCCG
 951 TGACCTTCAA  GCCACTGCCC  CGCTCACAGC  TATCTTGAGT  GCTGTCGTTG
1001 GCGCGGCAAA  GAGCGTGAAC  CGCAAGACCA  AACCATATGT  TATGGTCAAG
1051 GTCAGTCCGG  ATGAAGACTC  AGATGAACAA  GTCTCTGGTA  TCTGCGACGC
1101 CGTCCGAGCA  TCCGGTGTCG  ACGGAGTGAT  TGTCGGAAAC  ACAACAAACC
1151 GTCGCCCCGA  CCCTATACCC  CAAGGTTACA  CTCTTCCGGC  CAAGGAGCAG
1201 GCAACGTTGA  AAGAAACCGG  CGGGTATTCA  GGTCCACAGC  TGTTCGATCG
1251 CACAGTGGCC  CTTGTGGCTC  GGTACCGCTC  CATGCTGGAT  GCGGAGTCGG
1301 AAACGGCCGG  ATCCGCCAAG  GATTCAGCAG  CGACCATAGC  GCAAACAGAG
1351 CCAGGCTCGG  AAAACGTTCC  TCCTGTGGAA  GCGCCAAGCG  GACTGCCGCG
1401 CAAAGTTATC  TTCGCTTCGG  GTGGTATCAC  CAACGGGAAG  CAGGCTCACG
1451 CTGTTTTAGA  CACAGGGGCA  TCTGTTGCCA  TGATGTACAC  CGGTGTGGTC
1501 TATGGTGGCG  TCGGCACTGT  CACTCGAGTG  AAGCAAGAAC  TTCGAACGGC
1551 GAAAAAGGAG
```

The amino acid sequence encoded by the preferred resistance gene is:

```
  1 MATNSFRKLT  FSGASRLGGC  RRLPLTCRQL  RFASDSGAAA  ATTKATAESA
 51 AESASINVKE  APKKAGRGLR  RTVLGTSLAL  TLLVGYVYGT  DTRASVHRYG
101 VVPLIRALYP  DAEDAHHIGV  DTLKMLYKYG  LHPRERGDPD  GDGALATEVF
151 GYTLSNPIGI  SGGLDKHAEI  PDPLFAIGPA  IVEVGGTTPL  PQDGNPRPRE
201 FRLPSQRAMI  NRYGLNSKGA  DHMAAILEQR  VRDFAYANGF  GAYDAAKQRV
251 LDGEAGVPPG  SLQPGKLLAV  QVAKNKATPD  GDIEAIKRDY  VYCVDRVAKY
301 ADILVVNVSS  PNTPGLRDLQ  ATAPLTAILS  AVVGAAKSVN  RKTKPYVMVK
351 VSPDEDSDEQ  VSGICDAVRA  SGVDGVIVGN  TTNRRPDPIP  QGYTLPAKEQ
401 ATLKETGGYS  GPQLFDRTVA  LVARYRSMLD  AESETAGSAK  DSAATIAQTE
451 PSENVPPVE   APSGLPRKVI  FASGGITNGK  QAHAVLDTGA  SVANMYTGVV
501 YGGVGTVTRV  KQELRTAKKE
```

Another mutation of the DHOD gene giving rise to CCFQ resistance changes the cytidyl residue at position 344 of the intron-less coding sequence and the intron-containing sequence to a thymidyl residue, thus changing amino acid 115 from alanine to valine. The DNA sequence of this resistance gene is:

```
  1  ATGGCTACGA ATTCTTTCCG AAAACTCACT TTTTCAGGAG CCTCCCGTCT

51  GGGTGGTTGT CGCCGTCTCC CACTAACCTG CAGACAACTT CGATTCGCCT

101  CCGACAGCGG AGCCGCAGCG GCAACTACAA AAGCAACGGC CGAATCAGCA

151  GCCGAGTCAG CTAGTATAAA CGTCAAAGAG GCACCCAAAA AGGCCGGACG

201  GGGCCTGCGG CGCACGGTCC TGGGAACGTC GTTGGCGCTG ACGCTGCTGG

251  TTGGATATGT CTACGGGACG GACACCCGGG CGAGTGTGCA TCGGTACGGT

301  GTTGTGCCGC TGATTAGAGC ATTGTATCCT GATGCGGAAG ATGTGCATCA

351  TATTGGTGTC GATACTTTAA AGATGCTGTA TAAGTATGGT CTGCATCCAA
                                                          *
401  GGGAACGGGG GGATCCGGAT GGAGATGGGG CGCTGGCGAC AGAGGTGGGT
```

```
 451  GGTCTTTTAT TGTGATGGAA GTTAAGGCCC TAATACTTAT GGCGGATAGG

501  TCTTTGGGTA TACACTGTCA AACCCAATTG GCATATCGGG CGGCCTGGAC

551  AAGCATGCTG AGATCCCTGA TCCGCTGTTC GCGATCGGTC CTGCCATTGT

601  CGAAGTCGGG GGTACGACAC CCTTACCACA GGATGGTAAC CCGCGTCCTC

651  GCGTATTCCG ACTTCCATCA CAGAGAGCGA TGATAAACCG GTACGGCCTC

701  AACTCCAAAG GCGCAGATCA CATGGCAGCT ATCTTGGAGC AACGAGTACG

751  CGATTTTGCC TACGCAAACG GATTTGGGGC ATACGATGCG GCTAAGCAGC

801  GTGTATTGGA CGGCGAAGCT GGTGTGCCAC CAGGTAGTCT TCAGCCTGGT

851  AAGCTTTTAG CTGTCCAAGT GGCAAAGAAC AAGGCCACTC CTGACGGCGA

901  CATTGAAGCC ATCAAGCGCG ACTATGTGTA TTGCGTGGAC CGTGTGGCCA

951  AATACGCTGA TATTCTTGTT GTGAATGTAT CGAGCCCCAA CACACCCGGT

1001  CTCCGTGACC TTCAAGCCAC TGCCCCGCTC ACAGCTATCT TGAGTGCTGT

1051  CGTTGGCGCG GCAAAGAGCG TGAACCGCAA GACCAAACCA TATGTTATGG

1101  TCAAGGTCAG TCCGGATGAA GACTCAGATG AACAAGTCTC TGGTATCTGC

1151  GACGCCGTCC GAGCATCCGG TGTCGACGGA GTGATTGTCG GAAACACAAC

1201  AAACCGTCGC CCCGACCCTA TACCCCAAGG TTACACTCTT CCGGCCAAGG

1251  AGCAGGCAAC GTTGAAAGAA ACCGGCGGGT ATTCAGGTCC ACAGCTGTTC

1301  GATCGCACAG TGGCCCTTGT GGCTCGGTAC CGCTCCATGC TGGATGCGGA

1351  GTCGGAAACG GCCGGATCCG CCAAGGATTC AGCAGCGACC ATAGCGCAAA

1401  CAGAGCCAGG CTCGGAAAAC GTTCCTCCTG TGGAAGCGCC AAGCGGACTG

1451  CCGCGCAAAG TTATCTTCGC TTCGGGTGGT ATCACCAACG GGAAGCAGGC

1501  TCACGCTGTT TTAGACACAG GGGCATCTGT TGCCATGATG TACACCGGTG

1551  TGGTCTATGG TGGCGTCGGC ACTGTCACTC GCGTGAAGCA AGAACTTCGA

1601  ACGGCGAAAA AGGAG
```

The coding sequence (with the intron removed) is:

```
  1  ATGGCTACGA ATTCTTTCCG AAAACTCACT TTTTCAGGAG CCTCCCGTCT

51  GGGTGGTTGT CGCCGTCTCC CACTAACCTG CAGACAACTT CGATTCGCCT

101  CCGACAGCGG AGCCGCAGCG GCAACTACAA AAGCAACGGC CGAATCAGCA

151  GCCGAGTCAG CTAGTATAAA CGTCAAAGAG GCACCCAAAA AGGCCGGACG

201  GGGCCTGCGG CGCACGGTCC TGGGAACGTC GTTGGCGCTG ACGCTGCTGG

251  TTGGATATGT CTACGGGACG GACACCCGGG CGAGTGTGCA TCGGTACGGT

301  GTTGTGCCGC TGATTAGAGC ATTGTATCCT GATGCGGAAG ATGTGCATCA

351  TATTGGTGTC GATACTTTAA AGATGCTGTA TAAGTATGGT CTGCATCCAA

401  GGGAACGGGG GGATCCGGAT GGAGATGGGG CGCTGGCGAC AGAGGTCTTT

451  GGGTATACAC TGTCAAACCC AATTGGCATA TCGGGCGGCC TGGACAAGCA

501  TGCTGAGATC CCTGATCCGC TGTTCGCGAT CGGTCCTGCC ATTGTCGAAG

551  TCGGGGGTAC GACACCCTTA CCACAGGATG GTAACCCGCG TCCTCGCGTA

601  TTCCGACTTC CATCACAGAG AGCGATGATA AACCGGTACG GCCTCAACTC

651  CAAAGGCGCA GATCACATGG CAGCTATCTT GGAGCAACGA GTACGCGATT
```

```
701   TTGCCTACGC AAACGGATTT GGGGCATACG ATGCGGCTAA GCAGCGTGTA

751   TTGGACGGCG AAGCTGGTGT GCCACCAGGT AGTCTTCAGC CTGGTAAGCT

801   TTTAGCTGTC CAAGTGGCAA AGAACAAGGC CACTCCTGAC GGCGACATTG

851   AAGCCATCAA GCGCGACTAT GTGTATTGCG TGGACCGTGT GGCCAAATAC

901   GCTGATATTC TTGTTGTGAA TGTATCGAGC CCCAACACAC CCGGTCTCCG

951   TGACCTTCAA GCCACTGCCC CGCTCACAGC TATCTTGAGT GCTGTCGTTG

1001  GCGCGGCAAA GAGCGTGAAC CGCAAGACCA AACCATATGT TATGGTCAAG

1051  GTCAGTCCGG ATGAAGACTC AGATGAACAA GTCTCTGGTA°TCTGCGACGC

1101  CGTCCGAGCA TCCGGTGTCG ACGGAGTGAT TGTCGGAAAC ACAACAAACC

1151  GTCGCCCCGA CCCTATACCC CAAGGTTACA CTCTTCCGGC CAAGGAGCAG

1201  GCAACGTTGA AGAAACCGG CGGGTATTCA GGTCCACAGC TGTTCGATCG

1251  CACAGTGGCC CTTGTGGCTC GGTACCGCTC CATGCTGGAT GCGGAGTCGG

1301  AAACGGCCGG ATCCGCCAAG GATTCAGCAG CGACCATAGC GCAAACAGAG

1351  CCAGGCTCGG AAAACGTTCC TCCTGTGGAA GCGCCAAGCG GACTGCCGCG

1401  CAAAGTTATC TTCGCTTCGG GTGGTATCAC CAACGGGAAG CAGGCTCACG

1451  CTGTTTTAGA CACAGGGGCA TCTGTTGCCA TGATGTACAC CGGTGTGGTC

1501  TATGGTGGCG TCGGCACTGT CACTCGAGTG AAGCAAGAAC TTCGAACGGC

1551  GAAAAGGAG
```

The amino acid sequence encoded by this resistance gene is:

```
1    MATNSFRKLT FSGASRLGGC RRLPLTCRQL RFASDSGAAA ATTKATAESA

51   AESASINVKE APKKAGRGLR RTVLGTSLAL TLLVGYVYGT DTRASVHRYG

101  VVPLIRALYP DAEDVHHIGV DTLKMLYKYG LHPRERGDPD GDGALATEVF

151  GYTLSNPIGI SGGLDKHAEI PDPLFAIGPA IVEVGGTTPL PQDGNPRPRV

201  FRLPSQRAMI NRYGLNSKGA DHMAAILEQR VRDFAYANGF GAYDAAKQRV

251  LDGEAGVPPG SLQPGKLLAV QVAKNKATPD GDIEAIKRDY VYCVDRVAKY

301  ADILVVNVSS PNTPGLRDLQ ATAPLTAILS AVVGAAKSVN RKTKPYVVVK

351  VSPDEDSDEQ VSGICDAVRA SGVDGVIVGN TTNRRPDPIP QGYTLPAKEQ

401  ATLKETGGYS GPQLFDRTVA LVARYRSMLD AESETAGSAK DSAATIAQTE

451  PGSENVPPVE APSGLPRKVI FASGGITNGK QAHAVLDTGA SVAMMYTGVV

501  YGGVGTVTRV KQELRTAKKE
```

As those skilled in the art will recognize the present invention allows to generate other mutant DHOD genes at will. Given the DNA sequence for the DHOD gene, procedures familiar to skilled artisans are used to generate mutant DHOD enzymes that vary from the natural DHOD enzyme at any number of amino acid residue positions. Such mutant enzymes would be encoded by mutant DHOD coding sequences, including sequences in which amino acid codons have been deleted from or inserted into the natural DHOD coding sequence. Such mutant DNA sequences are within the scope of the present invention, because even if one cannot predict absolutely whether a given mutation will affect activity of the encoded DHOD, one may quickly use routine procedures to ascertain whether a mutation gives rise to a CCFQ resistance-conferring DNA sequence.

Furthermore, the present invention is not limited to isolated DNA sequences comprising an entire mutant DHOD gene. Because fungal recombinant DNA vectors can integrate into the fungal genome by homologous recombination, the only limitation on the resistance-conferring DNA sequence is that it be capable of conferring resistance to CCFQ when integrated into the wild-type DHOD gene. This event readily occurs even when only a portion of the DHOD gene is encoded by the recombinant DNA vector. See Examples, infra.

The mutant DHOD genes of the present invention are useful in any fungus which is sensitive to CCFQ and where the mechanism of action of CCFQ involves dihydroorotate dehydrogenase. Preferred fungi are Aspergillus, Penicillium, Cephalosporium and Neurospora. Preferred species of these fungi are *Aspergillus nidulans, Penicillium chrysogenum, Cephalosporium acremonium* and *Neurospora crassa*.

Those skilled in the art will recognize that the DNA sequences depicted above are an important part of the present invention. The above sequences can be conventionally synthesized by the modified phosphotriester method using fully protected deoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765. In addition, an especially preferred method is disclosed in Hsiung et al., 1983, Nucleic Acid Research 11:3227 and Narang et al., 1980, Methods in Enzymology 68:90. In addition to the manual procedures referenced above, the DNA sequence can be synthesized using automated DNA synthesizers, such as the ABS (Applied Biosystems, 850 Lincoln Centre Drive, Foster City, Calif. 94404) 380B DNA Synthesizer. The DNA sequence can also be generated by the polymerase chain reaction. See, e.q., U.S. Pat. Ser. Nos. 4,800,159 and 4,683,202 and European Patent Publication No. 0258017, published Mar. 2, 1987.

The amino acid sequences depicted above can be encoded by a multitude of different DNA sequences because most of the amino acid residues are encoded by more than one DNA triplet. Because these alternate DNA sequences would encode the same amino acid residue sequences of the present invention, the present invention further comprises these alternate sequences.

The present invention comprises DNA compounds and recombinant DNA cloning and expression vectors that comprise CCFQ resistance-conferring DNA sequences. The preferred CCFQ resistance-conferring sequences of the present invention were isolated from mutated strains of *A. nidulans*. A genomic library of the total genomic DNA of a mutated *A. nidulans* strain was constructed and examined for the presence of CCFQ resistance-conferring DNA sequences.

The preferred CCFQ resistance-conferring gene can be isolated on an ~8.3 kb partial SalI fragment derived from plasmid pGAR150, which has been deposited with the Northern Regional Research Laboratories (NRRL), Peoria, Ill. 61604, in *E. coli* K12 HB101 under the accession number NRRL B-18692. A restriction site and function map of plasmid pGAR150 is presented in FIG. 2 of the accompanying drawings. The ~7.3 kb SalI and ~5.4 kb HindIII restriction fragments of pGAR150 also confer resistance to CCFQ, but do not comprise the entire mutant DHOD gene.

Plasmid pGAR150 serves as useful starting material for the construction of other vectors of the invention. These vectors are especially useful in a method for constructing a recombinant host cell resistant to CCFQ, said method comprising transforming a host cell with a recombinant DNA vector that comprises an isolated DNA sequence which imparts resistance to CCFQ.

The following Examples are provided to further illustrate and exemplify, but not limit the scope of the present invention.

EXAMPLE 1

Mutagenesis of *Aspergillus nidulans*

The growth medium for *A. nidulans* is 33.6 g malt extract agar (Difco Laboratories, P.O. Box 1058, Detroit, Mich. 48232) plus 6 g agar (Gibco Laboratories, P.O. Box 68, Grand Island, N.Y. 14072) per liter of media. To grow *A. nidulans* FGSC610, add 1 ml of 1 mg/ml p-aminobenzoic acid (filter sterilized) per liter of media. To grow *A. nidulans* FGSC612, add 10 ml of 0.25 ml/ml riboflavin (filter sterilized) per liter of media.

A. Mutagenesis of *A. nidulans* FGSC612 with MNNG

*A. nidulans* FGSC612 was obtained from the Fungal Genetic Stock Center (FGSC), (University of Kansas Medical Center, Kansas City, Kans. 66103). A filter sterilized 1 mg/ml solution of N-methyl-N'-nitro-N-nitrosoguanidine (MNNG, Sigma Chemical Co., P.O. Box 14508, St. Louis, Mo. 63178) was prepared in neutral phosphate buffer (NPB). NPB is 4 g NaCl, 0.1 g $MgSO_4.7H_2O$, 7 g $Na_2HPO_4$ and 3 g $KH_2PO_4$ (pH 7.2) per liter of water and is filter sterilized. Eighteen ml of NPB were placed into each of four 50 ml test tubes labelled A, B, C and D. To each tube was added $10^8$ *A. nidulans* FGSC612 conidia in 1 ml Tween/saline (0.08% NaCl, 0.025% Tween 20). The tubes were placed at 37° C. Nineteen ml of MNNG were added to tubes A, B and C and 19 ml of NPB were added to tube D as a control. Tube A was removed after 30 minutes incubation at 37° C.

The spores were collected by centrifugation in a swinging bucket rotor at 16000×g for 10 minutes. All but about 1–1.5 ml of the supernatant was drawn off. The remainder of the supernatant and the spores were transferred to a 1.5 ml Eppendorf tube. The contents of the tube were subjected to microcentrifugation for 5 minutes. All but about 100 μl of the supernatant was then drawn off. The spores were resuspended in 1 ml NPB. The spores were again subjected to microcentrifugation and washed twice more in NPB. The final spore pellet was resuspended in 200 μl NPB. After 45 minutes at 37° C., the contents of tube B were treated as above. After 60 minutes at 37° C., the contents of tubes C and D were subjected to the above treatment.

The spores from each tube were divided and spread on two plates of *A. nidulans* growth medium containing 2.5 μg/ml CCFQ. CCFQ was made according to procedures described in European Patent Publication No. 326330, published Aug. 2, 1989. The plates were incubated at 370° C. Resistant colonies appeared in 3-4 days. The spores from tube D indicated the rate of spontaneously resistant mutants which was <1 per $10^8$ spores as compared to mutagenized *A. nidulans*, which was approximately 1 per $10^6$ spores. The *A. nidulans* mutant comprising the preferred CCFQ resistance gene was prepared as described above.

B. Mutagenesis of *A. nidulans* FGSC610 with EMS

*A. nidulans* FGSC610 was obtained from the FGSC. Conidia ($10^8$) of *A. nidulans* in 1 ml Tween/saline were added to each of four test tubes, labelled A, B, C and D, containing 29 ml of NPB at 37° C. Ninety μl of methanesulfonic acid ethyl ester (EMS; Sigma Chemical Co., P.O. Box 14508, St. Louis, Mo. 63178) (final concentration of EMS=0.3%) were added to tubes A, B and C and all tubes were incubated at 37° C. The remainder of the procedure was identical to Example 1A except that tube A was incubated for 30 minutes, tube B was incubated for 60 minutes and tubes C and D were incubated for 120 minutes. This procedure yielded a mutant comprising the resistance gene containing a thymidyl residue at position 344 of the dihydroorotate dehydrogenase gene.

EXAMPLE 2

A. Preparation of Cosmid Libraries

Libraries were prepared from the DNA of mutants of *Aspergillus nidulans* constructed as described above. Chromosomal DNA was partially digested with restriction enzyme Sau3AI and inserted into BamHI-digested cosmid pKBY2. The insert size ranged from approximately 33–40 kilobase pairs. Cosmid pKBY2 is available from the ATCC under accession number 39898. A restriction site and function map of pKBY2 is provided in FIG. 1. All of the procedures used in the preparation of the libraries are standard to skilled artisans.

B. Isolation of CCFQ Resistance Genes

Cosmids were combined into groups of 24 and analyzed for their ability to transform *A. nidulans* FGSC237 to resistance to 1.5 μg/ml CCFQ A single cosmid was then isolated that also transformed *A. nidulans* FGSC237 to CCFQ resistance.

The *A. nidulans* transformations were carried out as described below.

C. *A. nidulans* Transformation Procedure

A 1-liter baffled flask containing 400 ml of glucose minimal media (see below) plus any necessary supplements was inoculated with $4 \times 10^8$ *A. nidulans* conidia. The culture was grown for approximately 15 hr at 30° C. and 250 rpm. The stage of the culture is critical. The mycelium should be light and fluffy looking. Protoplasts derived from overgrown cultures (small mycelial balls) transform much less efficiently.

The mycelia were harvested by filtration through Miracloth (Calbiochem Corp., P.O. Box 12087, San Diego, Calif. 92112) and washed with 200 ml of sterile water. The mycelia were transferred to a 50 ml conical tube and resuspended in 40 ml of 1.2M MgSO4/10mM NaPO$_4$ (pH 5.8) by shaking and vortexing. Seventy-five mg of Novozyme 234 (Novo Nordisk Biolabs, Inc.) and 0.75 ml of beta-glucuronidase (Sigma Chemical Co.) were added to the mycelia and the mixture was incubated with slow rotation at 27° C. for 1.5–2.0 hr. The amount of Novozyme required can vary with the batch obtained from the supplier and the incubation time can vary between experiments. Protoplasting was monitored microscopically at timed intervals to insure optimum results. Vortexing the protoplast solution for a few seconds can reduce clumping and improve protoplast yield. Equal volumes of the protoplast solution were transferred into two 30 ml Sarstedt tubes and carefully overlayed with 8 ml of sterile ST buffer (ST=0.6M sorbitol/0.1M Tris-HCl, pH 7.0). The tubes were centrifuged at 4,000×g for 15 min at 20° C. in a swinging bucket rotor. Protoplasts were harvested from the interface and washed two times in 4 volumes of STC buffer (STC=1.2M sorbitol/10mM CaCl2/10mM Tris-HCl, pH 7.5). After each wash the protoplasts were recovered by centrifugation at 1,500×g for 10 min at 20° C. in a swinging bucket rotor. The protoplasts were resuspended in 1 ml of STC, counted in a haemocytometer and adjusted to a final concentration of $2 \times 10^8$/ml. For transformation, 2–5 μg of DNA in less than 10 μl of water was added to 150 μl ($3 \times 10^7$) protoplasts in a 1.5 ml Eppendorf tube. DNA and protoplasts were mixed and incubated at room temperature for 15 min. One ml of a polyethyleneglycol (PEG) solution (see PTC below) was then added and the solutions were thoroughly mixed and allowed to stand at room temperature for 15 min. The tubes were centrifuged for 4 min and as much as possible of the PEG solution was removed from the protoplast pellet. Protoplasts were resuspended in 1 ml of sterile YGS media (YGS=0.5% yeast extract/2.0% glucose/1.2M sorbitol) containing any supplements necessary for fungal growth and incubated at 27° C. for 2-3 hr with slow rotation. Cells were harvested by centrifugation for 3 min and resuspended in 150 μl of STC. 50 μl of this suspension were used to inoculate a single petri plate. The media on which the transformed fungi were selected consisted of glucose minimal media containing 1.2M sorbitol, any supplements that a transformed cell would need for growth (e.g., p-aminobenzoic acid was added to the media for transformations of strain FGSC237 with pKBY2-based vectors, but tryptophan was not added because any FGSC237 cell transformed with a cosmid containing pKBY2 should no longer require tryptophan) and 1.5 μg/ml CCFQ.

Plates were incubated at 37° C. for 3–5 days. For transformations that resulted in very few CCFQ resistant colonies, spores from those colonies were replated on media containing CCFQ to insure that the resistance trait was stable. PTC solution is 60% polyethylene glycol (British Drug Houses)/4000 10 mM CaCl$_2$/10 mM Tris-HCl, pH 7.5). The solution was filter sterilized and stored at –20° C. in 5–10 ml aliquots.

| Glucose minimal media (liquid) | |
|---|---|
| Trace Elements Solution | |
| FeSO$_4$.7H$_2$O | 1.00 g/liter |
| ZnSO$_4$.7H$_2$O | 8.80 g/liter |
| CuSO$_4$.5H$_2$O | 0.40 g/liter |
| MnSO$_4$.4H$_2$O | 0.15 g/liter |
| Na$_2$B$_4$O$_7$.10H$_2$O | 0.10 g/liter |
| (NH$_4$)$_6$Mo$_7$O$_{24}$.4H$_2$O | 0.05 g/liter |
| Stock Salts Solution | |
| NaNO$_3$ | 60.0 g/liter |
| KCl | 5.2 g/liter |
| KH$_2$PO$_4$ | 15.2 g/liter |
| Trace elements solution | 10.0 ml/liter |
| Adjust pH to 6.5 | |

To make 200 ml of glucose minimal medium combine 40 ml of stock salt solution with 140 ml of H$_2$O and autoclave. Then add 10 ml of filter sterilized 20% glucose and 10 ml of filter sterilized 2% MgSO$_4$.7H$_2$O. Add p- amniobenzoic acid (paba), riboflavin, etc. as needed depending on the auxotrophic requirements of the *A. nidulans* strain being grown. For 250 ml of solid minimal media combine 25.0 ml of stock salts, 10 ml 20% glucose, 10 ml MgSO$_4$.7H$_2$O, 3.75 g agar and 205 ml H$_2$O. Autoclave to sterilize.

EXAMPLE 3

Analysis of CCFO Resistance Genes

A portion of the resistance gene isolated above was used as a probe to isolate a resistance gene from the library derived from *A. nidulans* treated with MNNG. This resulted in the isolation of the preferred resistance gene of the invention. A cosmid comprising this gene is called pGAR150 and can be obtained from the NRRL (Northern Regional Research Center (NRRL), Agricultural Research Service, U.S. Department of Agriculture, Peoria, Ill. 61604) in *E. coli* K12 HB101 under accession number NRRL B-18692.

Figure 2:
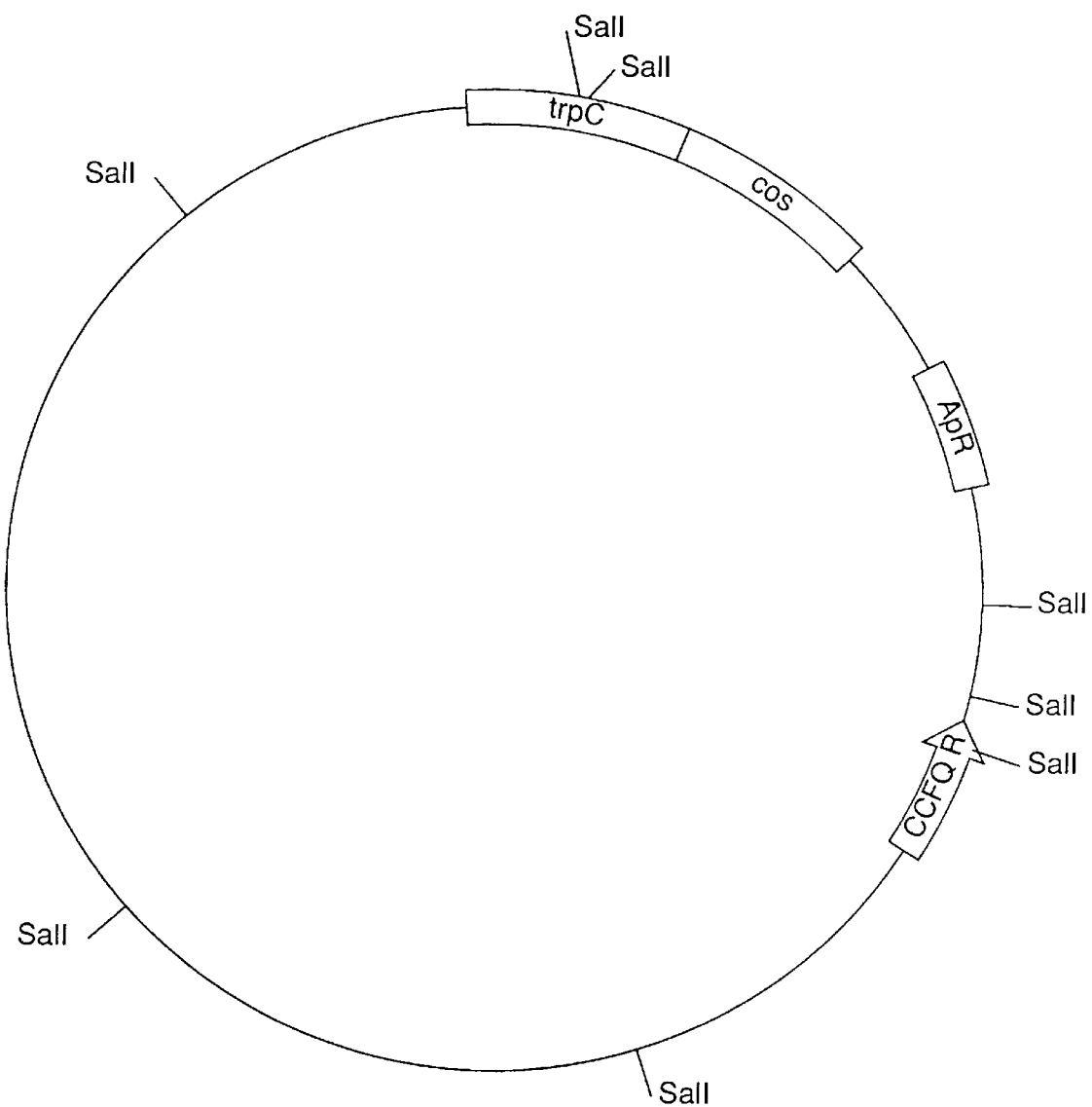
FIG. 2. A restriction site and function map of cosmid pGAR150.
Figure 3:
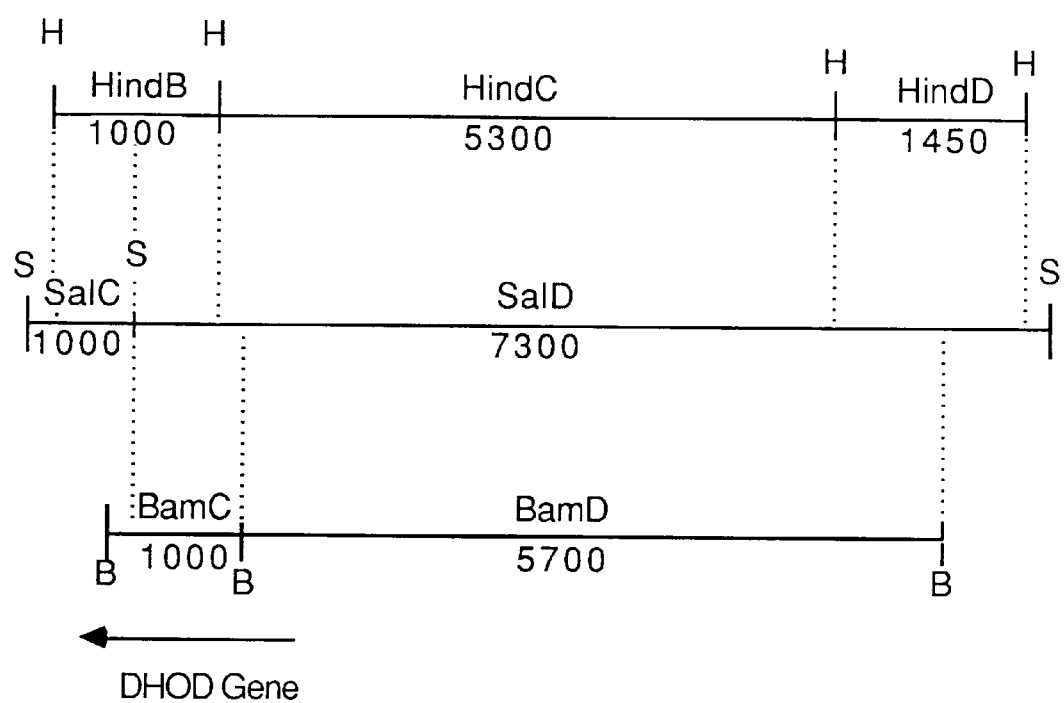
FIG. 3. A restriction map of the DHOD gene.

A restriction site and function map is presented in FIG. 2. A more detailed restriction map of the DHOD gene region is presented in FIG. 3.

Various restriction fragments derived from cosmids comprising resistance genes were cloned into pUC19 (Bethesda Research Laboratories, Inc., P.O. Box 577, Gaithersburg, Md. 20760) and tested for their ability to transform *A. nidulans* to CCFQ resistance. The transformations were carried out at described above. See FIG. 3 for an explanation of each fragment and placement of the gene.

TABLE I

| DNA Sample | CCFQ-resistant transformants/μg DNA |
|---|---|
| EMS treated DNA | |
| Entire cosmid | 35 |
| SalD | 6 |
| HindC | 3 |
| HindD | 0 |
| BamD | 1 |
| MNNG treated-DNA | |
| Entire cosmid | 60 |
| SalD | 8 |
| HindC | 6 |
| HindD | 0 |
| BamD | 0 |
| Wild-type gene containing cosmid | 0 |
| pUC19 | 0 |
| pKBY2 | 0 |

These results demonstrate that the entire open reading frame of the gene is not required to transform to CCFQ resistance.

We claim:

1. A method for identifying potential fungicides which comprises:
   (a) testing a candidate compound in a dihydroorotate dehydrogenase inhibition assay, and
   (b) if the candidate compound is active in the DHOD inhibition assay, testing the compound for activity against fungi.

2. The method of claim 1 including the additional step of, if the candidate compound is active in the DHOD inhibition assay, testing the candidate compound for activity against a second enzyme to eliminate the possibility that the compound is a general enzyme inhibitor.

3. The method of claim 2 wherein the second enzyme is *E. coli* alkaline phosphatase.

4. The method of claim 1 wherein the DHOD inhibition assay utilizes DHOD produced by *Pyricularia grisea*.

5. A method for identifying potential plant fungicides which comprises testing a candidate compound in a DHOD inhibition assay wherein the assay utilizes DHOD isolated from: *Pyrenophora Leres, Rhynchosporium secalis, Venturia inequalis, Alternaria mali, Rhizoctonia solani,* Fusarium sp., *Leptosphaeria nodorum, Pseudocercosporella herpotrichoides, Pyricularia oryzae, Pyricularla grisea, Phytophthora infestans*, Phytophthora sp., Pythium sp., *Mycospherella tritici*, or *Corticium sasakii*.

6. The method of claim 5 including the additional step of, if the candidate compound is active in the DHOD inhibition assay, testing the candidate compound for activity against a second enzyme to eliminate the possibility that the compound is a general enzyme inhibitor.

7. The method of claim 6 wherein the second enzyme is *E. coli* alkaline phosphatase.

8. The method of claim 5 wherein the DHOD inhibition assay utilizes DHOD produced by *Pyricularia grisea*.

* * * * *